(12) United States Patent
Sinnema et al.

(10) Patent No.: US 10,585,107 B2
(45) Date of Patent: Mar. 10, 2020

(54) DISH ROTATION DIRECTLY DRIVEN FROM TRANSPORT BELT

(71) Applicant: BD KIESTRA B.V., Drachten (NL)

(72) Inventors: Jurjen Sinnema, Joure (NL); Roger Petri, Assen (NL); Martijn Xander Berntsen, Leeuwarden (NL); Martijn Kleefstra, Surhuisterveen (NL)

(73) Assignee: BD KIESTRA B.V., Drachten (NL)

( * ) Notice: Subject to any disclaimer, the term of this patent is extended or adjusted under 35 U.S.C. 154(b) by 194 days.

(21) Appl. No.: 15/547,978

(22) PCT Filed: Feb. 4, 2016

(86) PCT No.: PCT/EP2016/052336
§ 371 (c)(1),
(2) Date: Aug. 1, 2017

(87) PCT Pub. No.: WO2016/124665
PCT Pub. Date: Aug. 11, 2016

(65) Prior Publication Data
US 2018/0045746 A1    Feb. 15, 2018

Related U.S. Application Data

(60) Provisional application No. 62/112,980, filed on Feb. 6, 2015.

(51) Int. Cl.
*G01N 35/02* (2006.01)
*G01N 35/04* (2006.01)
(Continued)

(52) U.S. Cl.
CPC ....... *G01N 35/00732* (2013.01); *C12M 23/10* (2013.01); *C12M 23/50* (2013.01);
(Continued)

(58) Field of Classification Search
None
See application file for complete search history.

(56) References Cited

U.S. PATENT DOCUMENTS

| 5,810,955 A | 9/1998 | Seifert et al. |
| 2004/0084531 A1 | 5/2004 | Teruaki |

(Continued)

FOREIGN PATENT DOCUMENTS

| JP | 07239333 A | 9/1995 |
| JP | 8104418 A | 4/1996 |
| JP | 2004156923 A | 6/2004 |

OTHER PUBLICATIONS

Japanese Notification of Reasons for Refusal issued in corresponding JP application No. 2017-559770 dated Sep. 27, 2018.
(Continued)

*Primary Examiner* — Kathryn Wright
(74) *Attorney, Agent, or Firm* — Botos Churchill IP Law LLP

(57) ABSTRACT

An apparatus for conveying a plurality of articles (10) includes a transport belt (6), a bumper stopper (14), and a rotator (12). A motor moves the transport belt which is adapted to rotate the rotator as the belt conveys the plurality of articles. The stopper can move between first and second positions relative to the transport belt wherein the bumper stopper guides one article toward the rotator when the bumper stopper is in the first position. The bumper stopper allows the article to be conveyed to another location when the bumper stopper is in the second position. The transport belt can continue to convey other articles while the one article is temporarily held in place by the bumper stopper. The rotator is configured to rotate the article conveyed by the transport belt. The article can remain in contact with the transport belt while the rotator is rotating the article.

8 Claims, 4 Drawing Sheets

(51) Int. Cl.
*G01N 35/00* (2006.01)
*C12M 1/22* (2006.01)
*C12M 1/00* (2006.01)

(52) U.S. Cl.
CPC ........... *G01N 35/021* (2013.01); *G01N 35/04* (2013.01); *G01N 2035/00752* (2013.01); *G01N 2035/0484* (2013.01)

(56) References Cited

U.S. PATENT DOCUMENTS

2010/0012460 A1    1/2010  Gianandrea
2010/0300831 A1*  12/2010  Pedrazzini ....... G01N 35/00732
                                                              198/339.1

OTHER PUBLICATIONS

International Search Report from PCT Application No. PCT/EP2016/052336 dated Apr. 4, 2016.

* cited by examiner

DISH ROTATION DIRECTLY DRIVEN FROM TRANSPORT BELT

CROSS-REFERENCE TO RELATED APPLICATIONS

The present application is a national phase entry under 35 U.S.C. 371 of International Application No. PCT/EP2016/052336 filed Feb. 4, 2016, published in English, which claims priority from of U.S. Provisional Application No. 62/112,980, filed Feb. 6, 2015, all of which are incorporated herein by reference.

BACKGROUND OF THE INVENTION

The present invention relates to a system to transport and identify an item under test such as a container used to evaluate a biological sample for the presence or absence of microorganisms (e.g. bacteria, fungi). Such containers are typically referred to as petri dishes or simply dishes. Such containers are also referred to as culture plates or simply plates.

Automated medical testing systems utilize a track to move the containers ("dish" hereinafter) for processing from one location to another. The dishes are inspected and identified at various locations as they are processed for testing and/or tracking. For example, the BD Kiestra® system offers multiple stations or modules or workbenches at which sample cultures in the dish undergo procedures and/or testing. Each dish must be identified before and/or after each such procedure or test to maintain accurate diagnostic records of the dish. Regular inspection of the dish ensures process integrity and ties all of the tests performed on the specific sample used to inoculate the culture media in the dish.

Previous methods of identifying a dish along the track utilize a barcode scanner and a scanning platform. The dish is stopped by mechanical means at a point along the track. A pneumatic cylinder raises the dish above a moving track and rotates the dish. A vacuum is provided to maintain the position of the dish on the cylinder. A barcode affixed to a side of the dish is scanned by the barcode scanner. The pneumatic cylinder then lowers the dish back onto the track to move the dish to another location.

The system for reading the barcode requires a multitude of moving parts to raise and rotate the dish. One motor is used to drive the transport belt and another motor to rotate the cylinder. The approach also increases the time needed to transport the dish from location to location because of the need to raise, scan, and lower the dish at each location where the dish is inspected.

Therefore, a need exists for an improved system of reading barcodes as dishes are transported from station to station in a multi-station processing system.

BRIEF SUMMARY OF THE INVENTION

One aspect of the disclosure describes an apparatus for reading a barcode comprising a dish having a barcode, a transport belt, a bumper stopper having a first position at a first distance from the transport belt and a second position at a second distance from the transport belt, a rotator, and a barcode scanner. In some embodiments, the transport belt moves the dish in a first direction toward the bumper stopper, and the bumper stopper contacts the dish when the bumper stopper is in the second position. The bumper stopper can deflect the dish in a second direction toward the rotator, and the rotator can align the dish with the barcode scanner.

The apparatus may comprise an actuator to move the bumper stopper between the first position and the second position. In some embodiments, the actuator may be a pneumatic cylinder. The apparatus may further comprise at least one guide rail adjacent the transport belt.

The rotator can comprise a disc and a shaft extending from the disc. The rotator may further comprise a contact surface extending circumferentially around the disc. The apparatus may further comprise a motor to drive the transport belt and may also include a drive train to couple the motor to a pulley wheel adapted to drive the transport belt. In some embodiments, the dish moves toward the rotator when the bumper stopper is in the second position.

One aspect of the disclosure describes an apparatus for reading a machine readable label affixed to a dish. The apparatus has a transport belt adapted to carry the dish with one machine readable label from location to location. The apparatus is equipped with a bumper stopper, a rotator having a shaft, a first pulley wheel coupled to the shaft, and a scanner. The transport belt is configured to both carry the dish and rotate the first pulley wheel to position the dish label for reading. The scanner reads the machine readable label when the dish is properly oriented for the label to be read.

In some embodiments, the bumper stopper moves between a first position and a second position with a component of motion transverse to the motion of the transport belt. The dish can move along a path and the bumper stopper may be at least partially within that path when the bumper stopper is in the second position. The bumper stopper can guide the dish into contact with the rotator. The apparatus may also include a plurality of second pulley wheels to align the transport belt. In some embodiments, the transport belt simultaneously carries the dish and rotates the first pulley wheel. The transport belt may comprise two generally parallel tracks. The tracks provide a stable and balanced surface used to carry the dishes. The belt configuration is largely a matter of design choice. The skilled person is aware of many different suitable belt configurations. Guard rails may be positioned adjacent the transport belt along the length of the transport belt.

Another aspect of the disclosure describes an apparatus comprising a means for moving a container, a means for temporarily stopping the container, a means for rotating the container, and a means for reading a barcode affixed to the container. The means for transporting the container may comprise a transport belt. The means for temporarily stopping the container and the means for rotating the container may oppose one another across the means for moving the container.

BRIEF DESCRIPTION OF THE DRAWINGS

A more complete appreciation of the subject matter of the present invention and the various advantages thereof can be realized by reference to the following detailed description, in which reference is made to the accompanying drawings.

DETAILED DESCRIPTION

Figure 1:
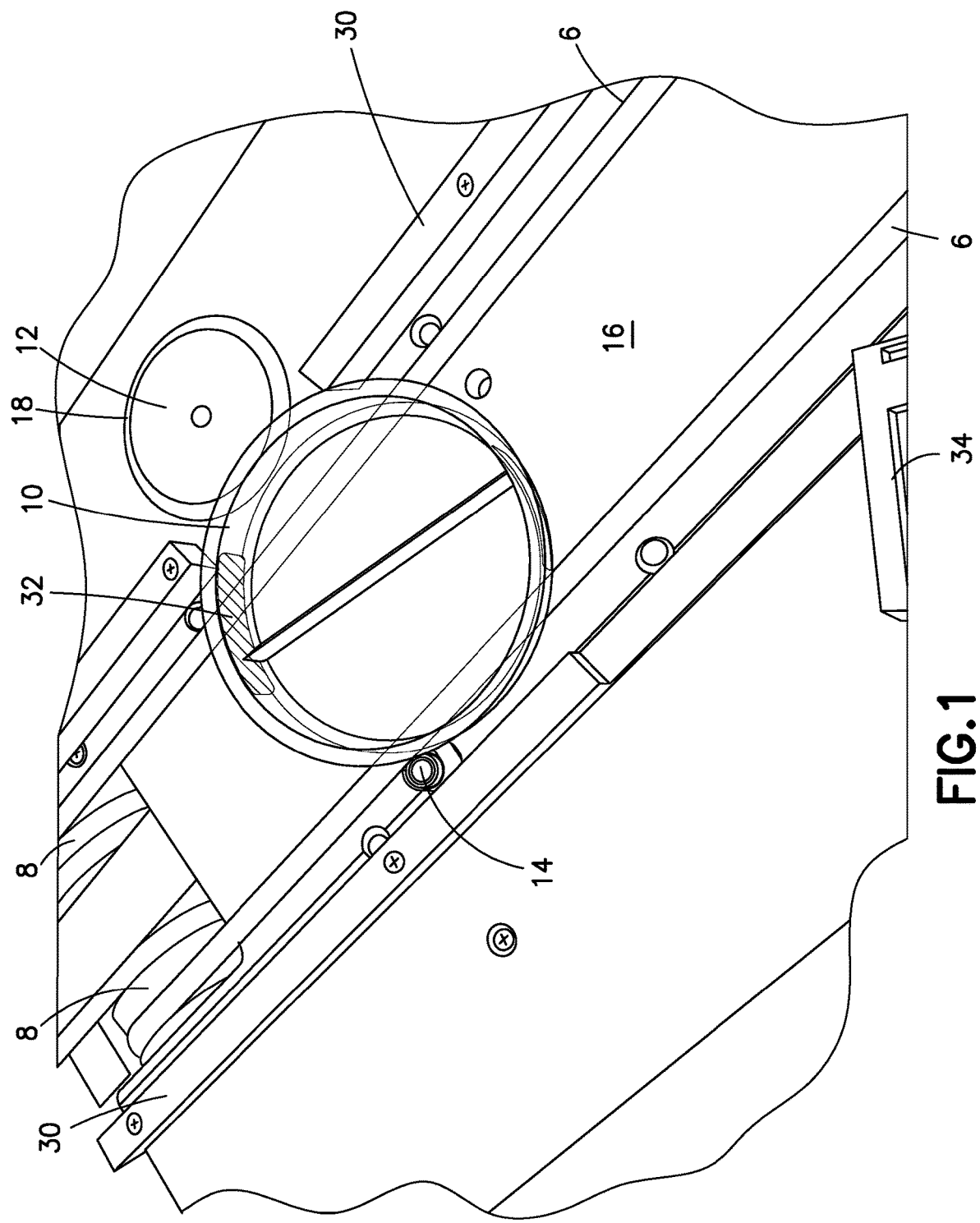
FIG. 1 is a perspective view of a transport belt, bumper stopper, rotator, and dish in accordance with one embodiment of the current invention.
Figure 2:
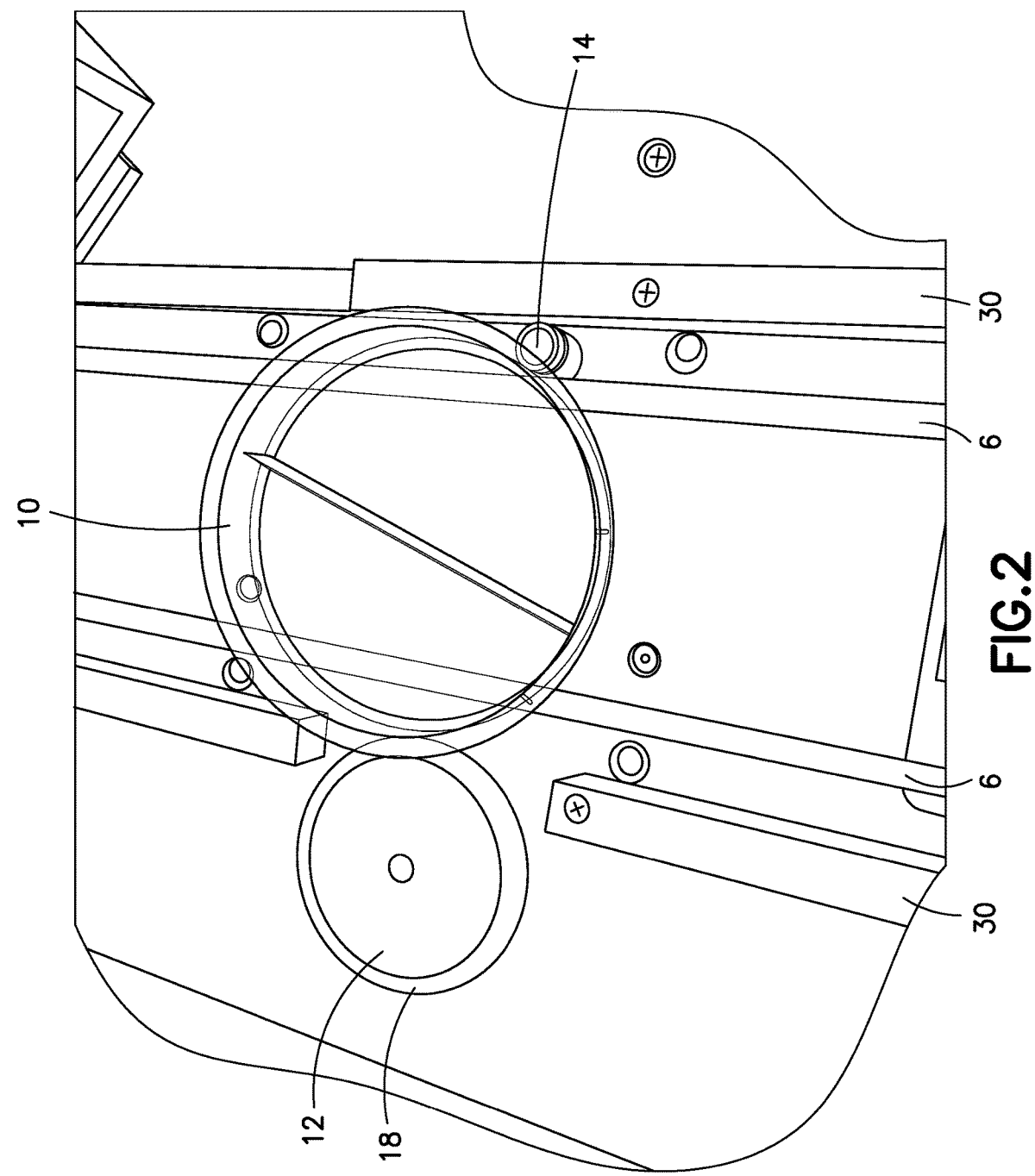
FIG. 2 is a rear perspective of the transport belt, bumper stopper, rotator, and dish of FIG. 1.
Figure 3:
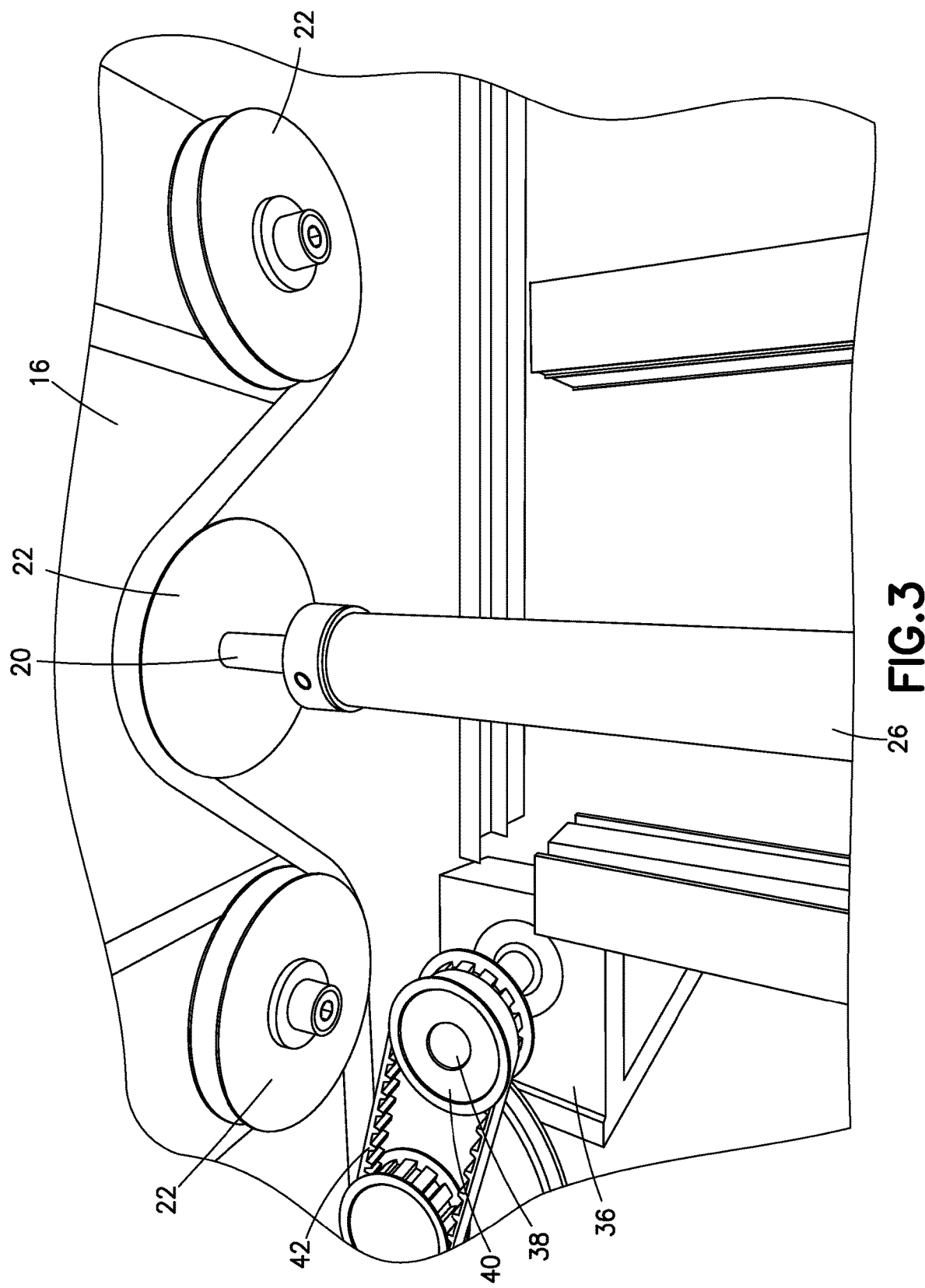
FIG. 3 is a bottom perspective view of pulley wheels, shaft, gear, timing belt, motor, motor shaft, and bearing in accordance with one embodiment of the current invention.

A barcode scanning apparatus according to one embodiment of the invention includes a transport belt 6 as shown in FIGS. 1-3. Transport belt 6 is shown as two generally parallel, spaced apart flexible belts which extend along an upper deck 16 of the conveyor. However, the transport belt could also be a single flexible or rigid conveyor belt or any number of different known belt designs and configurations. The present invention is not limited to a specific belt design or configuration. The "two belt" configuration described herein provides stable transport for the dishes described herein. The transport belt 6 is coupled to one or more pulley wheels 8. As explained in more detail below, the pulley wheels 8 may be driving members to rotate the transport belt 6. The transport belt is preferably a continuous member that forms a loop. Additional pulley wheels (not shown) may be positioned at a remote location along the upper deck at the end of the transport belt 6. The transport belt 6 extends around the pulley wheel 8 and through the upper deck 16.

The apparatus is adapted to convey a dish 10 which has a machine readable identifier 32 affixed to it. In the embodiment shown in FIGS. 1-2, the identifier is a one dimensional barcode. However, other machine readable identifiers are also possible (e.g. two dimensional barcode, RFID, EAS tag). The dish 10 shown is a conventional petri dish with a standard diameter (3.5 inches). However, the present invention can be adapted to convey any one of a number of different sample containers. When the transport belt is comprised of more than one individual belt, the distance between the belts is less than the diameter of the dish so that both belts support the dish.

A bumper stopper 14 is adjacent the transport belt 6. In the embodiment shown, the bumper stopper 14 is a pneumatic cylinder which extends through the upper deck 16. A bearing can be attached to the pneumatic cylinder to allow rotational motion about the cylinder axis. The pneumatic cylinder moves the bumper stopper 14 between a first position and a second position. In the first position, the proximal end of the bumper stopper 14 does not extend further from the upper deck 16 than the transport belt 6. In the second position, the bumper stopper 14 extends further above the upper deck 16 than the transport belt 6. The bumper stopper could also be configured to move from any direction in relation to the transport belt (e.g. from above, from the side).

A rotator 12 is adjacent the transport belt 6, preferably opposite the bumper stopper 14. In the embodiment shown, the rotator 12 is a disc with a shaft 20 extending from it (the shaft is best seen in FIG. 3). The rotator may have a contact surface 18 extending circumferentially about the disc. The contact surface may be a different material than the disc (e.g. rubber, plastic) to provide a high friction contact surface with the disc. The shaft 20 extends through the upper deck 16 and is coupled to a pulley wheel 22 such that rotation of the pulley wheel causes rotation of the shaft 20.

A scanner 34 is positioned in the vicinity of the transport belt 6 and rotator 12 (best seen in FIGS. 1-2). The scanner can be any scanner adapted to read machine readable identifiers (e.g. barcode scanner, RFID sensor, EAS detector). In the embodiment shown, a Microscan MS-3 Scanner is used. The scanner 34 can be positioned a distance from the transport belt 6 provided that the scanner is able to read the identifier from the distance at which it is placed.

One or more guide rails 30 extend along the path of the transport belt 6. As shown in FIGS. 1-2, the guide rail 30 is interrupted by the rotator 12. The guide rail 30 extends above the transport belt 6 to maintain the position of the dish 10 on the belt.

The transport belt 6 loops around the pulley wheel 8 and extends below the upper deck 16. As shown in FIG. 3, the transport belt 6 interweaves through pulley wheels 22. The pulley wheels 22 are secured to the bottom of the upper deck 16 by a fastener (e.g. screw, nut and bolt, rivet) which permit the pulley wheels to rotate about the fastener. The pulley wheels maintain the alignment of the transport belt 6 throughout the system. Shaft 20 is coupled to a bearing 26 which is attached to a surface 28 (best seen in FIG. 4) to secure the shaft 20 in place.

In some embodiments, the transport belt can be tensioned to maintain its position on the pulley wheels by first calculating the length of the path which the transport belt will travel. The length can then be multiplied by a reduction percentage (e.g. 6 to 10 percent, or more preferably, 8 percent). The transport belt can then be trimmed to that length and interweaved through the system described herein. The ends of the trimmed transport belt can then be attached to each other by welding, adhesive, or similar methods known to one of skill in the art.

Figure 4:
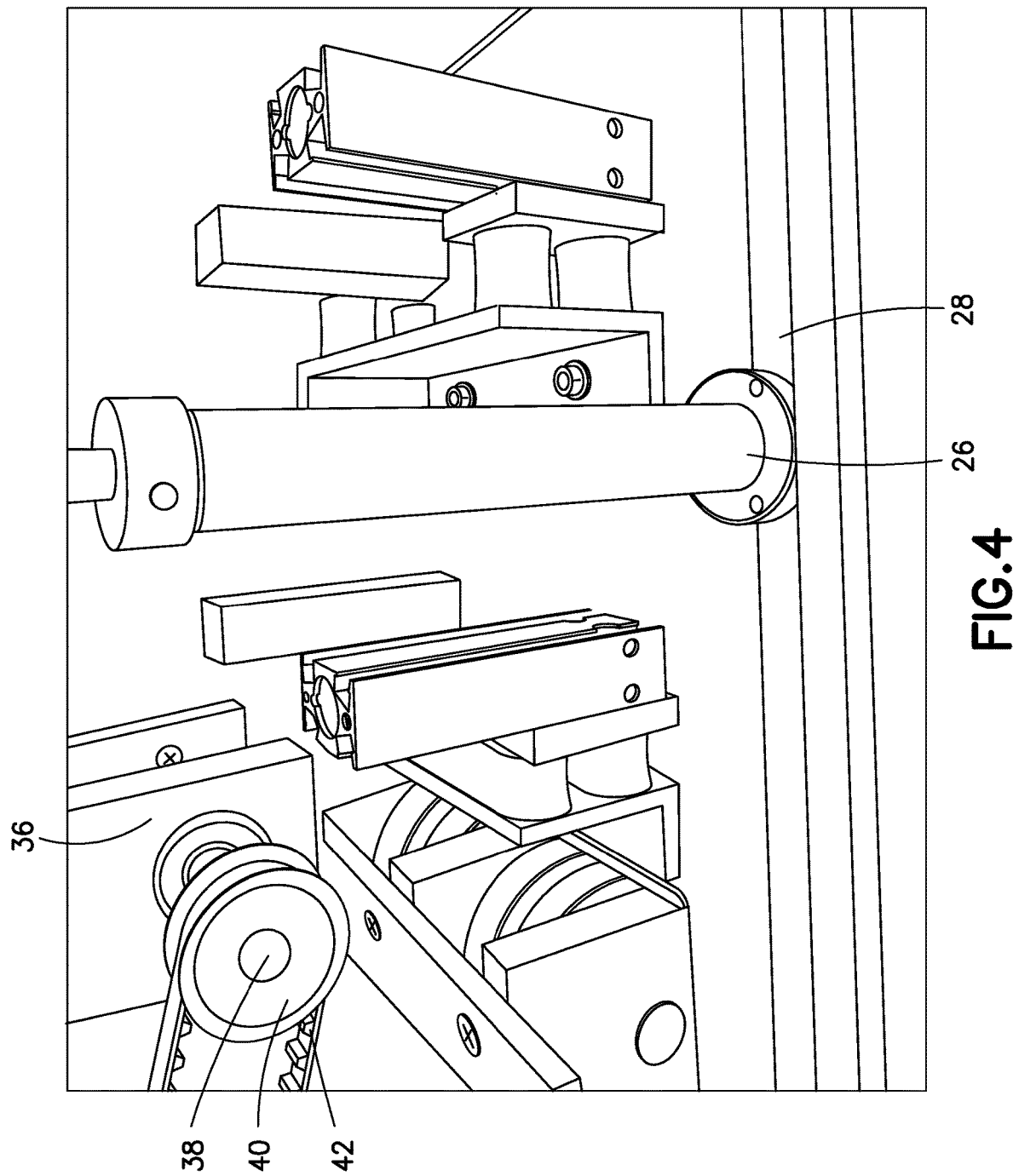
FIG. 4 is a perspective view of the cabinet floor, bearing, motor, motor shaft, gear, and timing belt in accordance with one embodiment of the current invention.

The transport belt is moved by a motor such as a Maxon Amax 11 W motor with an 84:1 gearbox. However, any suitable motor and gearbox are contemplated. The skilled person can select a motor suitable for use in the present invention. As shown in FIGS. 3-4, the motor 36 is positioned below the upper deck 16. The motor 36 may be coupled to the shaft (not shown) of the pulley wheel 8 by a drive train configured to transfer motion to the transport belt 6. For example, the motor shaft 38 is coupled to a gear 40. A similar gear could also be positioned on the pulley wheel shaft and a timing belt 42 transfers rotational motion between the shafts. Alternatively, the motor shaft could be in alignment with, and directly coupled to, the pulley wheel shaft, thereby eliminating the need for a gear and timing belt arrangement.

As the motor 36 transfers motion to the pulley wheel 8 via the drive train, the pulley wheel causes the transport belt 6 to move. The motion of the transport belt 6 moves the dish 10 toward the bumper stopper 14. The dish 10 contacts the bumper stopper 14 when it is in the second (raised) position. The transport belt continues to move and the stopper 14 does not fully impair movement of the dish 10 but instead guides the dish 10 toward the rotator 12.

The dish 10 contacts the first surface 18 of the rotator 12 as a result of the guidance from the bumper stopper 14. The rotator 12 is continuously rotating while the transport belt 6 is in motion because the transport belt 6 rotates the pulley wheel 22 and shaft 20. The rotator 12 rotates the dish 10 to align the machine readable identifier 32 with the scanner 34. The bearing on the bumper stopper 14 may rotate about its axis as the dish 10 rotates.

The rotator 12 can be configured to rotate at the same speed as the transport belt. The rotator speed can be faster or slower than the speed of the transport belt. Hence the rotator speed is largely a matter of design choice. The rotator speed is influenced at least in part by the scanner sensitivity. A faster scanner can allow for faster rotation of the dish. The dish is rotated at least one complete rotation by the rotator to ensure that the machine readable label on the dish is read regardless of where it is placed on the dish relative to the label's initial placement relative to the scanner. In one embodiment, the rotation takes about one to two seconds.

Once the identifier 32 has been read by the scanner 34, the pneumatic cylinder can move the bumper stopper 14 into the first position, allowing the dish 10 to be conveyed away by the transport belt 6. The scanner can be connected to a computer or electronic controller (e.g. microprocessor, PLC controller) that moves the bumper stopper once the barcode is read. If the scanner fails to read the barcode the bumper stopper can be configured to allow the dish to pass after a few seconds and mark the dish as "unknown". The guide rail 30 maintains the position of the dish 10 on the transport belt 6 as the dish continues to move with the belt.

The movement of the transport belt 6 is uninterrupted even when the dish 10 is temporarily held in place by the bumper stopper 14 and rotator 12. The continuous movement of the transport belt allows any other dishes on the belt to continue to be advanced in the apparatus while the machine readable identifier on a dish is being read, thereby confirming the identity of the dish under test.

In the embodiment shown in FIGS. 1-4, the rotator is driven by the transport belt. However, the rotator can also be driven independently of the transport belt so it can spin in both directions. This could be achieved by coupling a second motor to the rotator wheel.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An apparatus for conveying a plurality of dishes, the dishes carrying machine readable code, the apparatus comprising:

a transport belt that transports at least one dish through the apparatus;

a bumper stopper that, when in contact with a dish, stops the dish without stopping the belt;

a rotator comprising a disc and a shaft wherein the rotator causes the dish to spin when the dish is urged into contact with the rotator by the bumper stopper;

a first pulley wheel coupled to the shaft; and a reader;

wherein the transport belt is configured to advance the dish and rotate the first pulley wheel, thereby causing the shaft to rotate the disc; and wherein the reader reads the machine readable label as the transport belt continues to move.

2. The apparatus of claim 1, wherein the bumper stopper moves between a first position and a second position, wherein the movement has a component of motion transverse to the direction of travel of the transport belt.

3. The apparatus of claim 2, wherein the transport belt is configured to move the dish along a path and the bumper stopper in the second position is at least partially in the path.

4. The apparatus of claim 3, wherein the bumper stopper in the second position guides the dish into contact with the rotator.

5. The apparatus of claim 1, further comprising a plurality of second pulley wheels to align the transport belt.

6. The apparatus of claim 1, wherein the transport belt simultaneously moves the dish and rotates the first pulley wheel.

7. The apparatus of claim 1, wherein the transport belt comprises at least two generally parallel members.

8. The apparatus of claim 1, further comprising guard rails positioned adjacent to the transport belt extending along a length of the transport belt.

* * * * *